United States Patent [19]
Schaefer

[11] Patent Number: 5,911,688
[45] Date of Patent: Jun. 15, 1999

[54] BAGGAGE IDENTIFICATION SYSTEM USING CAPSULES ENCODED AND IDENTIFIED BY MEANS OF RADIO TRANSMISSIONS

[76] Inventor: Guenter Schaefer, 525 N. Ocean Blvd. #920, Pompano Beach, Fla. 33062-4630

[21] Appl. No.: 09/100,765

[22] Filed: May 7, 1998

Related U.S. Application Data

[62] Division of application No. 08/707,015, Sep. 3, 1996, Pat. No. 5,792,048.

[51] Int. Cl.[6] ........................................... A61B 5/00
[52] U.S. Cl. ..................... 600/302; 235/380; 235/487; 235/492
[58] Field of Search ..................... 600/302; 235/380, 235/487, 492

[56] References Cited

U.S. PATENT DOCUMENTS 5,792,048  9/1998  Schaefer .................................. 600/302

*Primary Examiner*—Harold I. Pitts
*Attorney, Agent, or Firm*—Ronald V. Davidge

[57] ABSTRACT

An electronic device fastened to a baggage item includes a microprocessor, data storage, radio circuits, and a radio antenna. When the baggage item is checked by a traveler at an airport, identification information corresponding to a code printed on the traveler's boarding pass is transmitted to the electronic device and recorded in its data storage. The traveler then proceeds to the gate of his flight, where the code printed on his boarding pass is read. The electronic device transmits stored identification information, so that the baggage item is loaded onto the aircraft only when the code printed on the boarding pass has been read at the gate.

9 Claims, 6 Drawing Sheets

5,911,688

BAGGAGE IDENTIFICATION SYSTEM USING CAPSULES ENCODED AND IDENTIFIED BY MEANS OF RADIO TRANSMISSIONS

CROSS-REFERENCE TO A RELATED APPLICATION

This application is a division of U.S. patent application Ser. No. 08/707,015 filed on Sep. 3, 1996 now U.S. Pat. No. 5,792,048.

FIELD OF THE INVENTION

This invention relates to a method for preventing the loading of a baggage item not accompanied by a traveler on an aircraft, and, more particularly, to an electronic device fastened to a baggage item in which an identification code is recorded, and from which the identification code is subsequently transmitted for comparison with a traveler's identification code read from a boarding pass at the area where the aircraft is boarded.

BACKGROUND OF THE INVENTION

Conventional airport baggage handling systems lack a means for preventing the loading of individual pieces of checked baggage belonging to a particular traveler onto an aircraft in the event that the traveler fails to board the aircraft, or if the traveler leaves the aircraft after boarding, making it possible for a traveler to have unaccompanied baggage placed on the aircraft.

What is needed is a method for tying each piece of checked baggage with the individual traveler checking it, and for permitting the loading of each such piece of checked baggage only after the traveler has entered a boarding area. Ideally, such a method would also provide for the rapid location of baggage of an individual traveler seeking to leave the aircraft or its boarding area.

SUMMARY OF THE INVENTION

A first objective of this invention is to provide a capsule, for placement within a piece of baggage, with a capability to receive and store a transmitted identification code, and to subsequently respond by transmitting this code.

A second objective of this invention is to provide a means for tying individual pieces of baggage to an individual traveller at baggage check-in within an airport.

A third objective of this invention is to provide a means whereby pieces of baggage checked by an individual traveler are held in a holding area until the individual traveler enters the aircraft.

DETAILED DESCRIPTION

Figure 1:
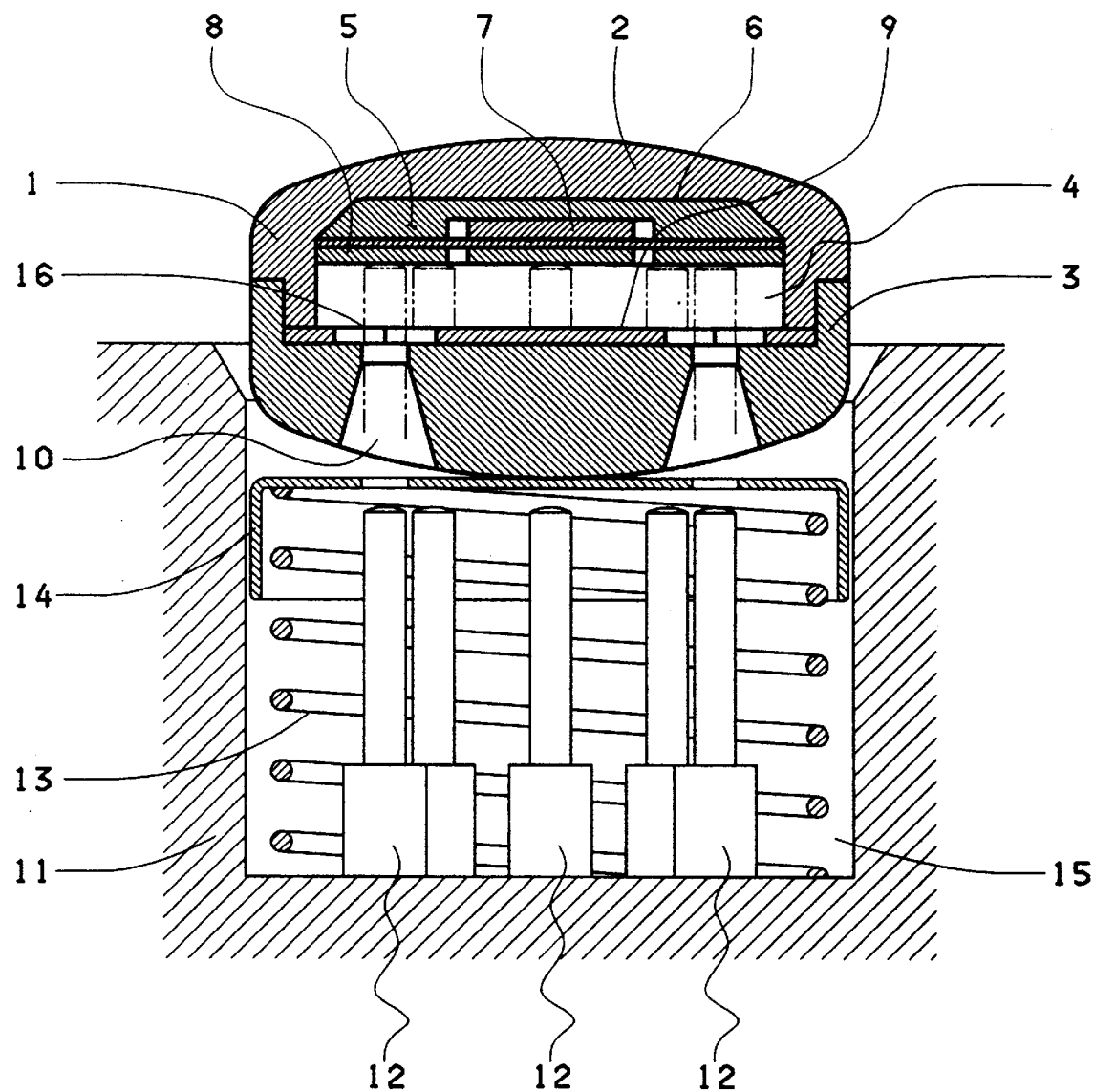
FIG. 1 is a longitudinal cross-sectional view of an identification pill built in accordance with a first version of the present invention.

FIG. 1 is a longitudinal cross-sectional view of an ingestible capsule 1, built in accordance with the present invention, within a device cavity providing electrical contact pins used for writing data into the ingestible capsule 1 and for reading data therefrom. This ingestible capsule 1 includes two acid-resistant plastic shells 2, 3. The upper plastic shell 2 has a shaped cavity 4 accommodating a plastic disc 5, which has on one side a metallic surface 6 that allows metal detectors to locate the ingestible capsule. The disk 5 is otherwise composed of an insulating plastic material.

A circuit chip 7, adapting to the shape of the identification pill 1, is embedded inside a small cavity of the plastic disc 5, which also acts as a carrier of contact tabs 8 attached to the circuit chip 7. The shaped cavity 4 is sealed by a plastic membrane 9, which can be penetrated by contact pins 12. After the retraction of the contact pins 12, the plastic membrane 9 seals itself and protects the circuit chip 7 with its contact tabs 8.

The lower plastic shell 3 is constructed with tapered penetration holes 10 which lead to the contact tabs 8. The lower plastic shell 3 is sealed to the upper plastic shell 2, holding the plastic membrane 8 in place. In the example of FIG. 1, the ingestible capsule 1 is shown with contact pins 12, extending upward within a cavity 15 of an external device 11, entering the tapered penetration holes 10. The ingestible capsule 1 is next pushed down over the contact pins 12, so that the contact pins 12 are brought into contact with contact pads 8. Data can then be read from, or written to, memory circuits within the ingestible capsule 1 through the contact pins 12. As the ingestible capsule 1 is pushed into the cavity 15, a carrier 14 is depressed, compressing a spring 13.

Figure 2:
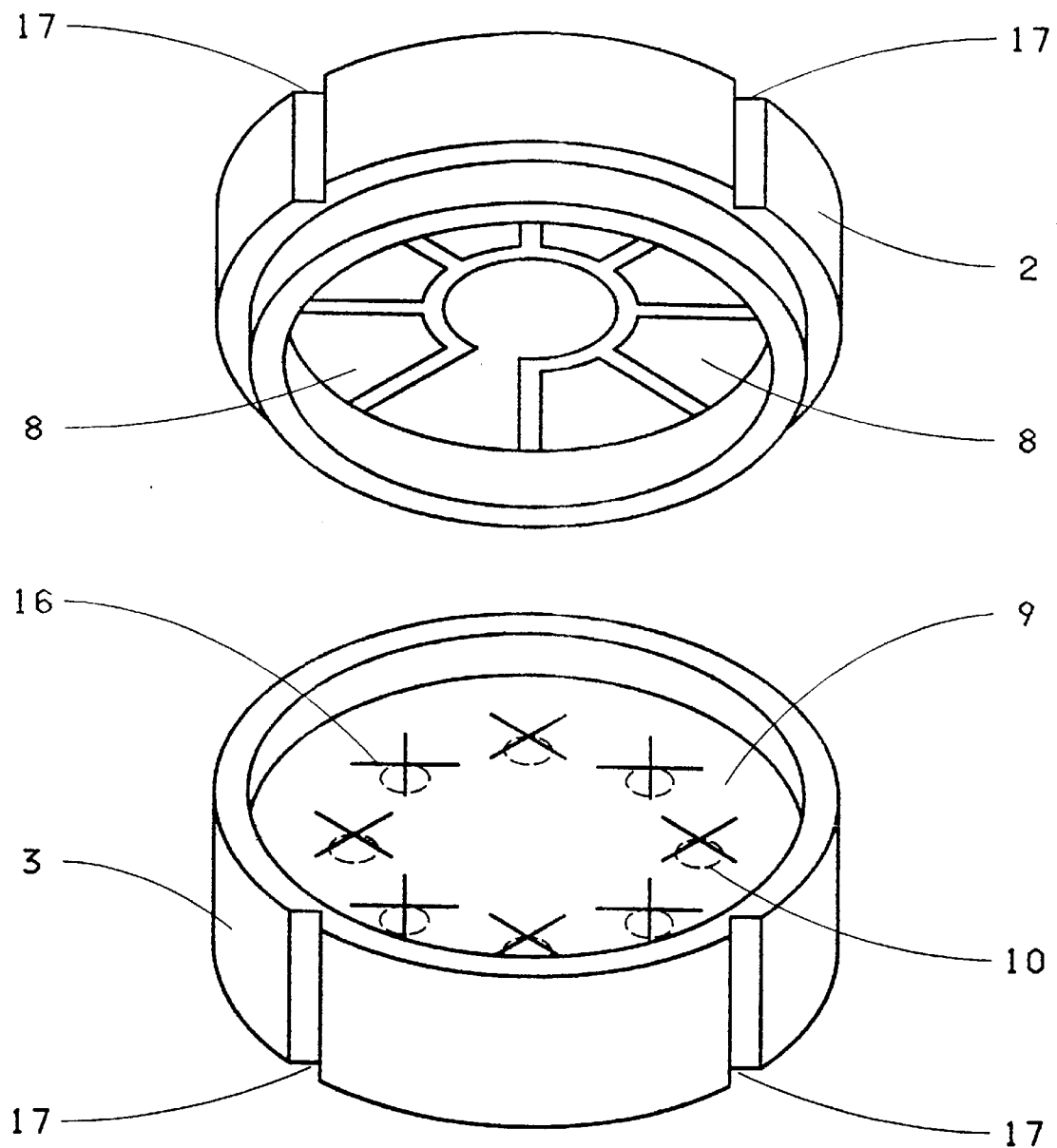
FIG. 2 is an isometric view of the identification pill of FIG. 1 in an opened condition.

FIG. 2 is an isometric view of the ingestible capsule 1 of FIG. 1 in an opened condition, exposing the contact tabs 8 of the circuit chip 7. The upper and lower plastic shells 2, 3 are key coded by features 17 to ensure positioning of all contact tabs 8 relative to penetration holes 10. The penetration holes IO for the contact pins 12 (shown in FIG. 1) are sealed by the plastic membrane 9. To facilitate penetration, the plastic membrane 9 can have When the contact pins 12 are removed, the flaps formed between the cross-cuts 16 return to their flattened condition, restoring the seal established using the plastic membrane 9.

When the ingestible capsule 1 is orally taken at the beginning journey it serves as an identification tablet, which is protected against heavy impacts and fire, which cannot be lost, and which provides identification data that can be recovered.

The circuit chip preferably includes a built in security code without which stored data cannot be changed.

Figure 3:
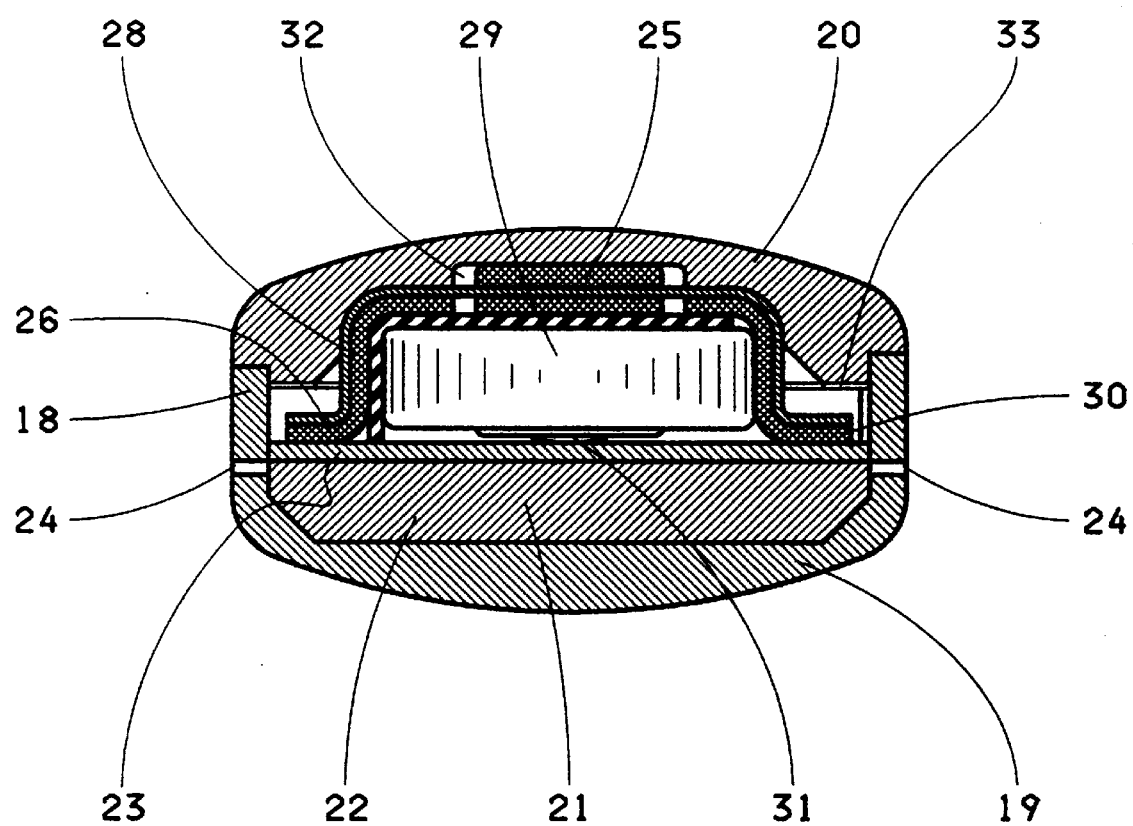
FIG. 3 is a longitudinal cross-sectional view of a miniature device built in accordance with a second version of the present invention, including a battery for powering mechanical devices needed in applications such as analysis, and for providing power needed for radio reception and transmission.

FIG. 3 is a longitudinal cross-sectional view of a miniature device 18 built in accordance with a second version of the present invention, which is enclosed by two acid-resistant plastic shells 19, 20. The lower plastic shell 19 has a cavity 21 in which a circuit board 22 is inserted. The circuit board accommodates micro mechanics, such as a combination of pumps, sensors, counters, motors, and other miniature devices (not shown) which support analytic instrumentation. The circuit board 22 is constructed with contact tabs 23 that engage the contact tabs 26, 30, 31 of a circuit chip with an integrated microprocessor 25. Certain contact tabs 23 also engage the contact surfaces of the battery 29. The circuit board may also include a reservoir for the storage of medicine caused to be measured and delivered by means of a pump and motor, at intervals as required, by programming the integrated microprocessor 25. Contacts to a device external to the miniature device 18 are made through holes or contacts 24, which are accommodated in the lower plastic shell 19. The molded cavity 32 of the upper plastic shell 20 is shaped to accommodate the microprocessor 25. The contact tabs 26, 30 of the microprocessor 25 are bent in such a way that a battery 29 with an insulating shell 28 can be accommodated, achieving power distribution to both the circuit board 22 and the microprocessor 25.

Adding an antenna 33 to the rim of the upper plastic shell 20 provides for two-way wireless communication, enabling an external device to call up the results of a process, and enabling an external device to transmit new instructions. This capability provides the miniature device 18 with an advantage of flexibility. The plastic shells 19, 20 are sealed at assembly. The miniature device 18 is also suitable for implantation into tissue or muscle. Miniature devices 18 for implantation can also be manufactured from suitable metals.

Figure 4:
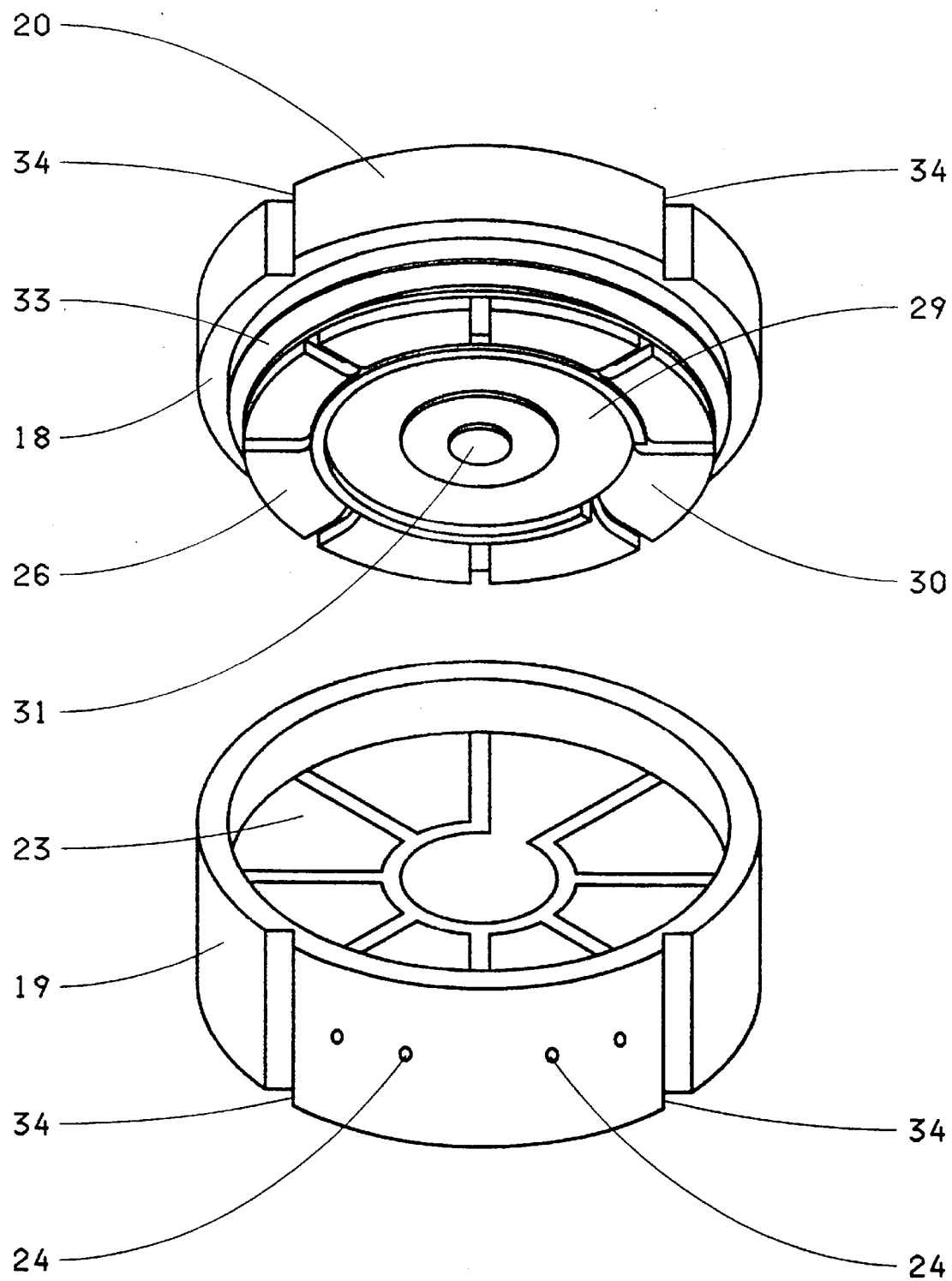
FIG. 4 is an isometric view of miniature device of FIG. 3.

FIG. 4 is an isometric view of the miniature device 18 of FIG. 3 in an opened condition. Plastic shells 19, 20 are coded by features 34 so that the relative positioning of the contact tabs 23, 26, 30, 31 is ensured. The position of the antenna 33, as well as that of the battery 29, are shown within the opened upper plastic shell 20. The contact tabs 23 of the circuit board 22 are shown within the opened lower plastic shell 19.

To increase safety against terrorism on airliners, the miniature device 18 can also be used to identify baggage, establishing a relationship between the baggage and the holder of a ticket and/or boarding card. In this application, a miniature device 18 with two-way radio communication capability is, for example, non-removably attached to the inside of each piece of the traveler's baggage. When the baggage is checked at the airport, each piece of baggage is tied to the ticket and/or boarding card, for example, with a bar code being printed on the ticket or boarding card as the information content in the bar code is transmitted by radio to the miniature device 18. This information is stored within the memory of the miniature device 18. The baggage is then moved from the baggage checking area to a holding area or waiting stage, such as a circulating conveyer belt. After the owner of the baggage has checked in for his flight at its gate, his ticket and/or boarding card is passed through an electronic reader, where the bar code is read. He then enters the airliner, with his baggage being cleared through identification information transmitted from the miniature device 18, so that the baggage can be loaded onto the airliner. In accordance with one version of the present invention, the traveler is not allowed to leave the airliner after this procedure. In accordance with another version of the present invention, should a traveler request or try to leave the airliner, his baggage is swiftly located. When a traveler changes from one airliner to another, his baggage can be checked through to the connecting airliner by transporting the baggage to the waiting stage for baggage of the connecting flight. This process prevents anyone from checking unaccompanied baggage onto a flight, reducing the threat of sabotage.

Figure 5:
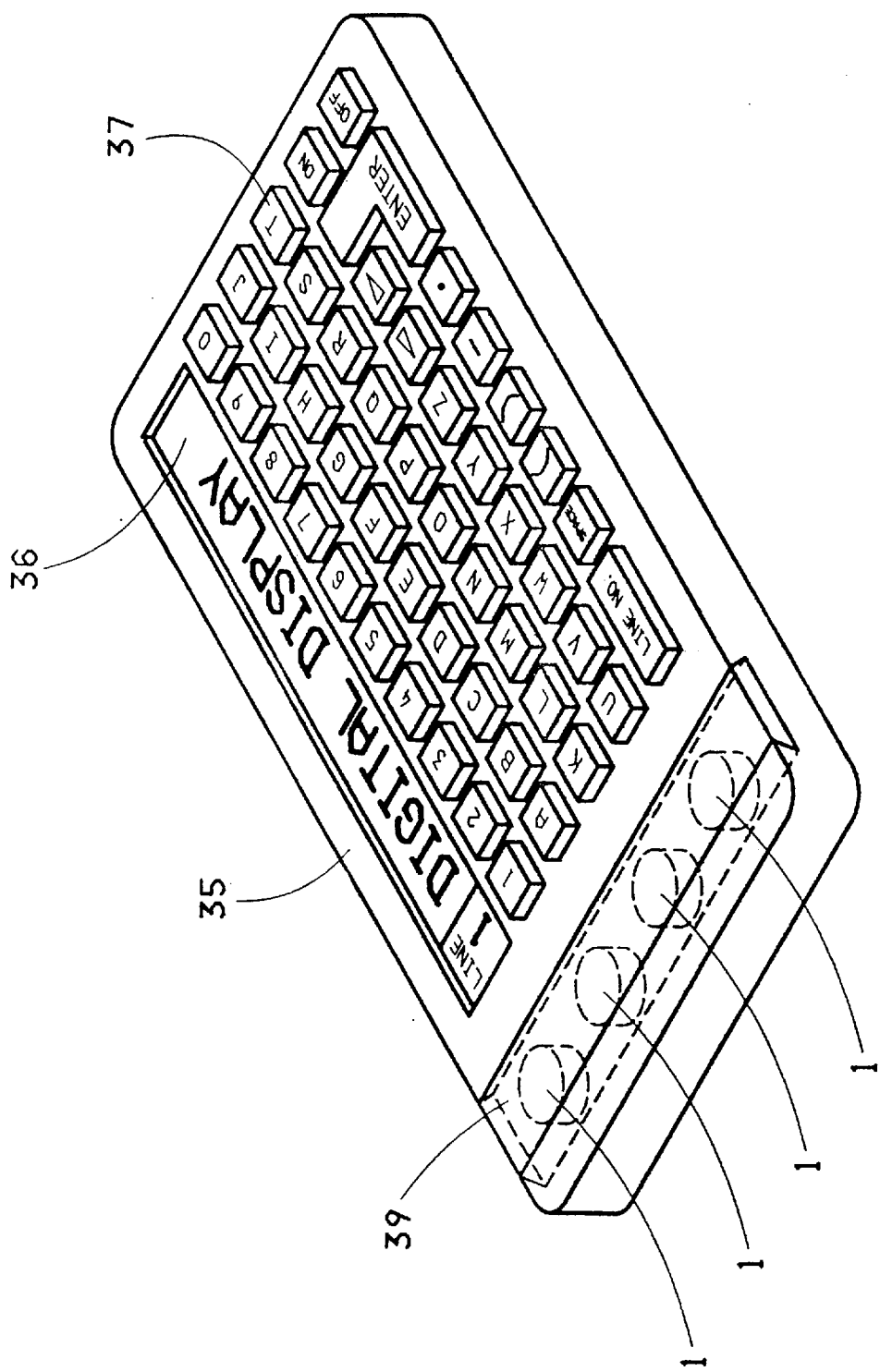
FIG. 5 is an isometric view of a stand-alone device for reading and writing data to the identification pill of FIG. 1.

FIG. 5 is an isometric view of a stand-alone device 35 for reading and writing data to and from the identification pill of FIG. 1. This stand-alone device 35 includes a digital display 36 and a keyboard 37. This stand-alone device 35 includes a number of cavities 15 having contact pins 12, as described above in reference to FIG. 1. When a cover 39 of the stand-alone device 35 is in the closed position shown in FIG. 5, the ingestible capsules I are pushed down to achieve contact with the contact pins 12. When the cover 39 is removed, the ingestible capsules 1 can be taken off the cavities 15 (shown in FIG. 1).

Figure 6:
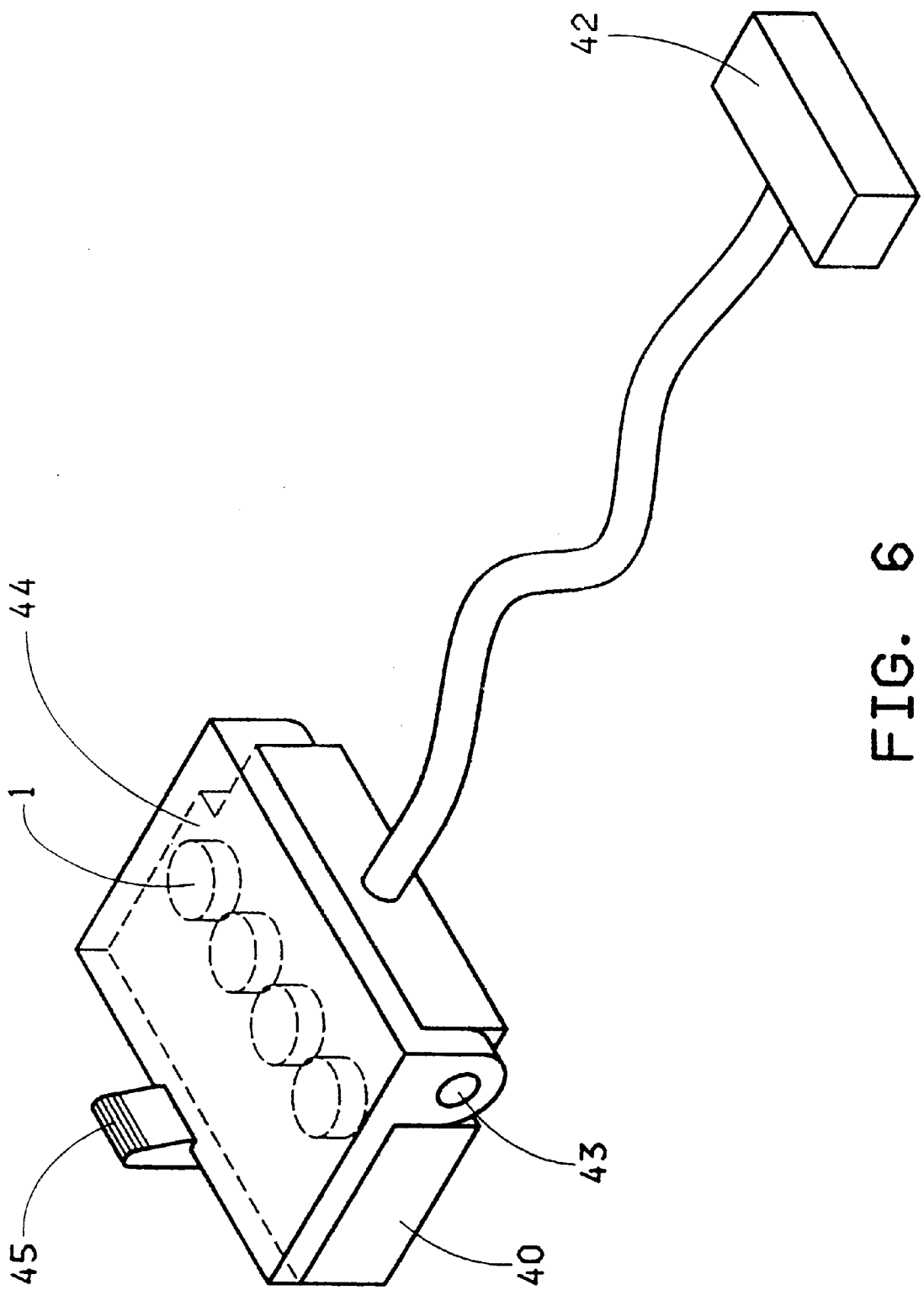
FIG. 6 is an isometric view of a peripheral unit for reading and writing data to the identification pill of FIG. 1 by means of software executing in a computing system.

FIG. 6 is an isometric view of a computer peripheral device 40, which can read data from the ingestible capsule 1, and write data thereto, in accordance with a software program executing in an external computer (not shown). The computer peripheral device 40 has integrated cavities 15, which are equipped with contact pins 12, as described above, in reference to FIG. 1. A cover 44, hinged on pins 43, holds a number of ingestible capsules 1 in contact with the contact pins 12 (shown in FIG. 1). When a snap 45 is released, the hinged cover 44 can be opened so that ingestible capsules 1 can be inserted or removed. The connector 41 is plugged to a computer (not shown).

What is claimed is:

1. An electronic device comprising:

an upper shell including an intermediate cavity extending upward within said upper shell from a lower surface of said upper shell and an upper cavity extending upward within said upper shell from said intermediate cavity;

a lower shell including a lower cavity extending downward within said lower shell from an upper surface of said lower shell;

a circuit board extending within said lower cavity, including a first plurality of contact surfaces extending along an upper surface of said circuit board;

a battery extending within said intermediate cavity, including a central contact terminal, wherein said central contact terminal extends downward in electrical contact with a first contact surface within said first plurality of contact surfaces;

an outer contact terminal, extending downward in electrical contact with a second contact surface within said first plurality of contact surfaces, wherein said battery establishes an electrical potential between said central terminal and said outer contact terminal;

a circuit chip including an integrated microprocessor circuit; and a second plurality of contact tabs extending downward from said circuit chip and around said battery to contact various contact surfaces within said first plurality of contact surfaces.

2. The electronic device of claim 1, additionally comprising:

a radio antenna; and radio circuits attached to said circuit board for transmitting and receiving signals through said radio antenna.

3. The electronic device of claim 2, wherein said upper and lower shells are each composed of acid-resistant thermoplastic materials, and said lower shell includes a plurality of apertures for electrical connections between said circuit board and a device external to said electronic device.

4. The electronic device of claim 2, wherein said electronic device additionally comprises data storage, said microprocessor writes an identification code into said data storage in response to a first radio signal providing said identification code, and said microprocessor causes said identification code stored within said data storage to be transmitted from said electronic device through said antenna.

5. A security system for tracking a plurality of baggage items to be loaded onto an aircraft, wherein said system comprises:

an electronic device attached to each baggage item within said plurality of baggage items, wherein said electronic device includes a microprocessor, data storage, an antenna, and radio circuits operating in response to said microprocessor to receive and transmit data, wherein identification data transmitted to said electronic device by a first radio signal is stored within said data storage, and wherein said identification data stored in said data storage is transmitted from said electronic device;

a data transmission station transmitting said first radio signal, wherein said identification data corresponds to identification information printed on a boarding pass;

a boarding pass reading station reading said identification information printed on said boarding pass; and a data receiving station receiving said identification data transmitted from said electronic device and releasing said baggage item to which said electronic device is attached only when said boarding pass, having said identification data corresponding to said identification data transmitted from said electronic device, has been read by said reading station.

6. The security system of claim 5, wherein said electronic device additionally includes:

an upper shell having an intermediate cavity extending upward within said upper shell from a lower surface of said upper shell and an upper cavity extending upward within said upper shell from said intermediate cavity, wherein a circuit chip including said microprocessor extends within said upper cavity;

a lower shell including a lower cavity extending downward within said lower shell from an upper surface of said lower shell;

a circuit board extending within said lower cavity, including a first plurality of contact surfaces extending along an upper surface of said circuit board and said radio circuits;

a battery extending within said intermediate cavity, including a central contact terminal, wherein said central contact terminal extends downward in electrical contact with a first contact surface within said first plurality of contact surfaces;

an outer contact terminal, extending downward in electrical contact with a second contact surface within said first plurality of contact surfaces, wherein said battery establishes an electrical potential between said central terminal and said outer contact terminal; and a second plurality of contact tabs extending downward from said circuit chip and around said battery to contact various contact surfaces within said first plurality of contact surfaces.

7. A method for tracking a baggage item to be loaded onto aircraft, wherein said method comprises steps of:

a) transmitting by radio an encoded signal including identification data corresponding to printed encoded information on a boarding pass;

b) receiving said encoded signal in an electronic device attached to said baggage item;

c) storing said identification data from said encoded signal within data storage of said electronic device;

d) reading said printed encoded information on said boarding pass at a location where a first aircraft is boarded;

e) transmitting by radio said identification data stored within said data storage; and f) releasing said baggage item to be loaded onto said first aircraft only when steps d) and e) have been completed.

8. The method of claim 7 additionally comprising, in the event a person having said boarding pass attempts to leave said aircraft, location of said baggage item by transmission therefrom of said identification data stored with data storage.

9. The method of claim 7, additionally comprising:

g) reading said printed encoded information on said boarding pass at a location where a second aircraft is boarded;

h) transmitting by radio said identification data stored within said data storage; and i) releasing said baggage item to be loaded onto said second aircraft only when steps h) and i) have been completed.

* * * * *